United States Patent [19]

Hötzel et al.

[11] Patent Number: 5,496,461
[45] Date of Patent: Mar. 5, 1996

[54] ELECTROCHEMICAL SENSOR FOR DETERMINING THE OXYGEN CONTENT IN GASES

[75] Inventors: Gerhard Hötzel, Stuttgart; Harald Neumann, Vaihingen; Walter Strassner, Schorndorf; Johann Riegel, Bietigheim-Bissingen, all of Germany

[73] Assignee: Robert Bosch GmbH, Stuttgart, Germany

[21] Appl. No.: 316,107

[22] Filed: Sep. 30, 1994

[30] Foreign Application Priority Data

Sep. 30, 1993 [DE] Germany ............... 43 33 230.7

[51] Int. Cl.$^6$ .................................................. G01N 27/26
[52] U.S. Cl. .................... 204/427; 204/425; 204/426; 204/408
[58] Field of Search .......................... 204/408, 425, 204/426, 427

[56] References Cited

U.S. PATENT DOCUMENTS

| | | | |
|---|---|---|---|
| 4,356,065 | 10/1982 | Dietz | 204/425 |
| 4,496,455 | 1/1985 | Linder et al. | 204/425 |
| 4,765,880 | 8/1988 | Hayakawa et al. | 204/425 |
| 4,859,307 | 8/1989 | Nishigawa et al. | 204/425 |

*Primary Examiner*—Bruce F. Bell
*Attorney, Agent, or Firm*—Walter Ottesen

[57] ABSTRACT

The invention relates to a measuring sensor having an internal pump oxygen reference atmosphere which, in turn, has a device for compensating pressure which is so dimensioned that, on the one hand, mechanical damage because of overpressure in the reference volume is reliably prevented and, on the other hand, external influences on the composition of the pumped measured gas atmosphere are substantially excluded. The device for compensating for pressure is so dimensioned according to the invention that the particle exchange between ambient air and gas to be measured is opposed by a resistance which is defined by the limit current principle.

5 Claims, 3 Drawing Sheets

$$U_s = U_n + R_i \cdot I_p$$

ELECTROCHEMICAL SENSOR FOR DETERMINING THE OXYGEN CONTENT IN GASES

FIELD OF THE INVENTION

The invention relates to an electrochemical sensor for determining the oxygen content in gases. The sensor has an internal oxygen reference.

BACKGROUND OF THE INVENTION

U.S. Pat. No. 4,496,455 discloses a sensor having an internal oxygen reference which operates according to the diffusion limit current principle disclosed in U.S. Pat. No. 4,356,065 (German patent publication 2,711,880).

This sensor includes a solid electrolyte made of zirconium dioxide. The solid electrolyte carries two pairs of electrodes permeable to oxygen and these electrodes are comprised, in part, of platinum.

One of the two electrode pairs in combination with the electrolyte defines the measuring cell. One of the two electrodes operates as a cathode and is indirectly exposed to the gas to be measured (measured gas) via a porous intermediate layer operating as a diffusion limiter. Oxygen molecules diffuse out of the gas to be measured to the cathode and are there catalytically split up into oxygen ions. The negative oxygen ions migrate to the anode under the influence of a voltage applied externally to the electrodes. In accordance with the limit-current principle, the voltage is so dimensioned that the intensity of the electric current carried by the oxygen ions is essentially dependent upon the rate at which the oxygen diffuses out of the gas to be measured to the measuring electrode. This rate is known to be dependent upon the oxygen concentration in the exhaust gas so that the diffusion limited current flow defines a measure for the composition of the measured gas.

The anode adjoins a small porous filled volume in order to maintain a constant oxygen partial pressure at the anode of the measuring cell. This constant oxygen partial pressure is desirable for measurement reasons and the volume is substantially insulated from the measured gas and from the ambient air.

Likewise, the anode of a second electrode pair borders on this volume. This second electrode pair together with the electrolyte and an externally applied voltage define a pump cell.

The cathode of the pump cell is exposed directly to the gas to be measured so that the pumped ion current is not limited by a diffusion boundary. The oxygen particles exiting at the anode of the pump cell form an internal reference atmosphere within the small porous volume.

Fine bores are provided to the gas to be measured in order to limit the pressure of this reference atmosphere to permissible values.

The above-mentioned patent publication provides no suggestion as to how or pursuant to what criteria the bores are to be dimensioned which act as a means to compensate for overpressure.

In this context, the following problem is presented. On the one hand, the pressure-limiting connection of the reference atmosphere to the measured gas must guarantee that no mechanical damage occurs to the sensor even for a short-term increased pump current. The connection must therefore make a certain minimum particle current possible.

If, on the other hand, the connection permits a particle current which is too great, then the reference atmosphere can become adulterated by the influence of the measured gas.

The measured gas can, for example, be the exhaust gas of an internal combustion engine. If this is the case, uncombusted fuel particles can diffuse out of the exhaust gas and into the reference gas volume. There, the fuel particles can bind oxygen and thereby considerably affect the oxygen partial pressure. This case can especially occur for a mixture composition rich in fuel or for an engine at standstill and with the pump voltage switched off. One conceivable remedy comprises increasing the pump current during operation of the engine so high that the oxygen particle current from the reference gas volume provides for a scavenging of the reference gas volume via the connection to the measured gas.

This advantage is offset in that a long-term increase of the pump current can lead to a decomposition of the electrolyte and therefore to a destruction of the sensor.

These problems can also occur when the overpressure compensation is not directed to the measured gas but is instead directed to the ambient air because the immediate ambient of the sensor can be exposed to fuel vapor or other impurities especially when the engine is at standstill.

SUMMARY OF THE INVENTION

In view of this background, it is an object of the invention to provide a sensor having an internal pumped oxygen reference atmosphere and a means to compensate for pressure which is so dimensioned that, on the one hand, mechanical damage from overpressures in the reference volume are reliably prevented and that, on the other hand, external influences on the composition of the pumped measured gas atmosphere are substantially excluded.

The measuring sensor of the invention is for determining the concentration of oxygen in a gas to be measured or measured gas and includes: a solid electrolyte; a measuring electrode arranged on the electrolyte so as to be subjected to the measured gas; a reference electrode arranged on the electrolyte; the solid electrolyte having holding means for holding a reference gas so as to expose the reference electrode to the reference gas; the holding means being arranged in the electrolyte so as to permit the reference gas to communicate with ambient air to allow a first particle exchange between the ambient air and the reference gas and for permitting a second particle exchange between the measured gas and the reference gas only via the electrolyte; overpressure compensating means interposed between the reference gas and the ambient air for defining a resistance opposing the first particle exchange; electric voltage means for applying a voltage of a first polarity across the electrodes during measurement for determining the concentration of oxygen in the measured gas by causing the second particle exchange as an oxygen ion flow from the measured gas to the reference gas; and, the resistance being defined by providing a diffusion limit current having a current intensity of 0.5 to 50 microampere when the voltage assumes a second polarity opposite the first polarity.

The oxygen ion current from the measured gas to the reference atmosphere, which is associated with the measuring current, should overcompensate the particle flow from the ambient to the reference gas volume. In this way, possible adulteration of the reference atmosphere during operation of the measuring sensor is avoided.

This condition can be satisfied for a typical configuration of the measuring sensor when the diffusion limit current does not exceed 50 microamperes.

If, however, adulteration occurs, then the particle exchange should not be hindered too much in order to make a scavenging of the reference gas volume possible such as by a temporarily increased pump current.

Typically, the measurement sensor exhibits a certain natural leakage rate (caused by the microporosity of the electrolyte or fault locations) which corresponds to a diffusion limit current in the order of magnitude of less than 0.5 microampere.

The ranges of 0.5 to 50 microampere and especially from 1 to 10 microampere have been shown to be advantageous for the typical application of detecting the oxygen content in the exhaust gas of an internal combustion engine. This has been achieved for the conditions which are present there and which include a sensor geometry determined by heat-up time and strength and cost.

When the measuring sensor is used as intended, the sensor supplies an electrical voltage in the order of magnitude of 1 Volt. The measurement of this voltage with a voltage measuring device leads to a measurement current of 1 microampere with the measuring device having an internal resistance of 1 megaohm. Since this measurement current is carried by oxygen ions within the electrolyte, the disadvantage is present without the resupply of oxygen from the reference gas volume, that the oxygen partial pressure will drop in the reference gas volume and the measurement will be falsified. The oxygen ions migrate from the reference gas volume to the measured gas. The pump current is impressed externally and supplies oxygen to the reference gas volume. This pump current advantageously is of a like order of magnitude.

The overpressure compensation must be able to allow this pump current to flow off to the ambient as required. In view of this background, a configuration of the means for compensating overpressure to a limit current intensity of approximately 3 microamperes has been shown to be advantageous.

The means for compensating the overpressure can, for example, be realized by a thin channel filled with porous material or by a porous input lead to the reference electrode.

The means for compensating for pressure defined in this manner makes possible a very weak low particle exchange by diffusion between the internal pumped oxygen reference atmosphere and the ambient air.

The influence of contaminants of the ambient air in the proximity of the measuring sensor on the reference gas atmosphere is significantly reduced compared to a measuring sensor having an air reference when the measuring sensor according to the invention is utilized for controlling the fuel/air ratio for an internal combustion engine driving a motor vehicle. Compared to an overpressure compensation to the exhaust gas of the engine, the measuring sensor of the invention affords the advantage that rich exhaust gas does not affect the reference gas atmosphere. For this reason, the pump current defined by the diffusion limit current can be limited to values for which no significant decomposition of the electrolyte occurs.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1A:
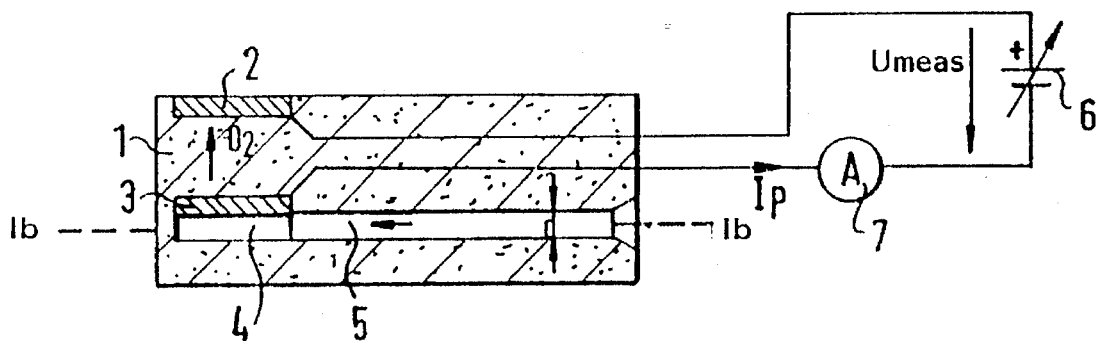
FIGS. 1a and 1b show a schematic of an embodiment of the measuring sensor according to the invention together with an electric circuit which facilitates quantitatively detecting the characteristic of the measuring sensor essential to the invention.
Figure 1B:
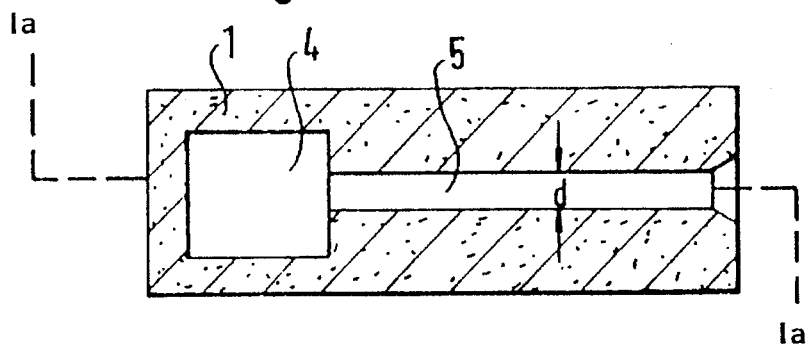

Reference numeral 1 in FIG. 1a identifies an oxygen ion conducting solid electrolyte taken along line Ia—Ia of FIG. 1b. The solid electrolyte 1 supports a measuring electrode 2 and a reference electrode 3. The reference electrode communicates with a reference atmosphere in a reference gas volume 4 within the measuring sensor. The thin porous filled channel 5 makes a defined but low particle exchange possible between reference atmosphere and ambient air.

FIG. 1b is a section view of the measuring sensor of FIG. 1a taken along the line Ib—Ib and rotated by 90°.

The measuring arrangement generates an electric field between the electrodes 2 and 3 which is so directed that the oxygen particles migrate to the measuring electrode. These oxygen particles dissociate catalytically to ions at the reference electrode.

The current flow associated therewith flows in the measuring current circuit comprising voltage source 6, amperemeter 7, electrodes 2 and 3 including the leads corresponding thereto and solid electrolyte 1. The current flow is registered by the amperemeter 7.

A reduction of the oxygen partial pressure is facilitated by the direction of the electric field. This reduction is counteracted by a resupply of oxygen from the ambient air via the thin porous filled channel 5.

For this purpose, the current resistance of the channel 5 is so dimensioned according to the invention that a limit current Ip in the order of magnitude of 1 to 10 microamperes flows from the measuring electrode to the reference electrode when a suitable pump voltage Umeas is applied with a voltage source 6. The current resistance of the channel 5 is dimensioned by means of its geometric dimensions (diameter d) and the characteristic of its charge (pore size).

Figure 2:
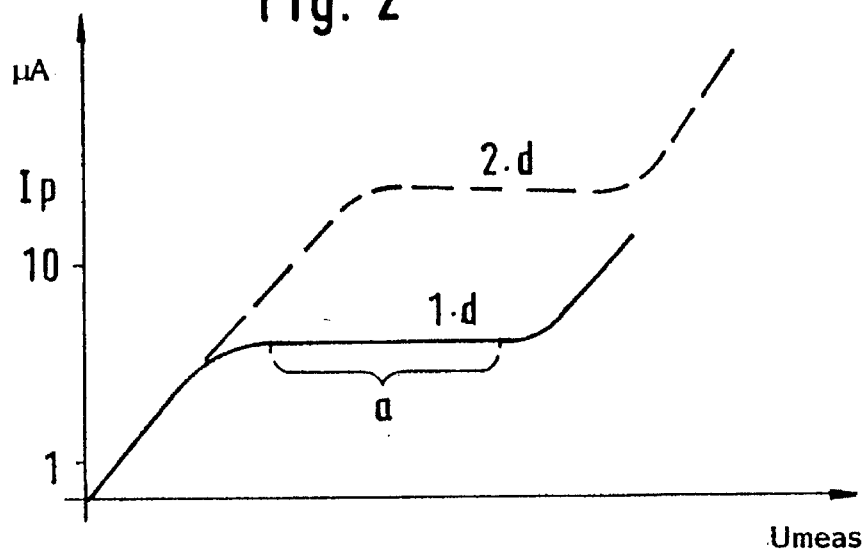
FIG. 2 is a graph of a current-voltage characteristic line for the arrangement of FIG. 1 with a parameter, which in the illustrated embodiment, codetermines the characteristic of the measuring sensor essential to the invention.

The solid line of the current-voltage characteristic in FIG. 2 shows a trace as it corresponds to the invention. This trace has a limit current plateau between 1 and 10 microampere.

This limit current is characterized in that the current intensity is determined by the number of oxygen particles diffusing to the electrode and not by the rate at which the oxygen molecules are dissociated into ions at the electrode.

If the electric field is strong enough to permit this particle count to flow off via the electrolyte, then a further increase of the field intensity does not provide an increase of the current intensity. The range (a) of the solid line in FIG. 2 emphasizes the invariance of the current changes or voltage changes.

Stated otherwise, the limit current Ip characterizes the intensity of the particle exchange between reference gas volume and ambient air. The resistance of a pressure compensation channel 5 having the thickness 1*d of a measuring sensor (which provides the characteristic shown by the solid line) is therefore selected according to the invention. If, in contrast, the thickness is changed to 2*d with other conditions remaining the same, a measuring sensor is obtained having a higher limit current value as shown by the broken line in FIG. 2. A limit current value which is too high corresponds to some extent to too strong a coupling of the composition of the reference gas atmosphere to the composition of the ambient air with the further disadvantages mentioned above.

Figure 3:
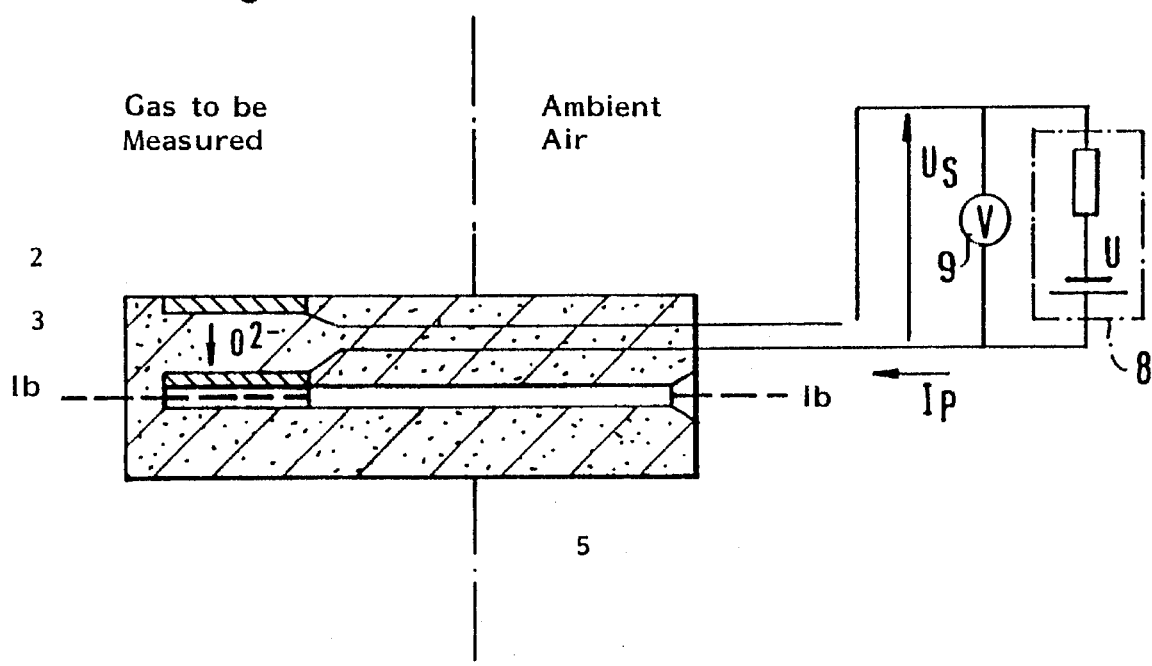
FIG. 3 shows the embodiment of the measuring sensor of FIG. 1 together with an electric circuit for a use of the measuring sensor.

FIG. 3 shows the measuring sensor of FIG. 1 together with a circuit suited for a particular use, that is, to measure the oxygen concentration in a gas to be measured (measured gas).

For this purpose, the measuring electrode 2 is connected to a minus pole and the reference electrode 3 to a positive pole of a current/voltage supply 8. A voltmeter 9 measures the signal Us of the measuring sensor which results in Us=Un+Ri.Ip in the arrangement shown; wherein: Ri is the internal resistance of the measuring sensor, Un is its Nernst voltage which results from the difference of the oxygen partial pressures in the measured and reference gases; and, Ip corresponds to the pump current.

In contrast to the arrangement of FIG. 1, the pump current is here so directed that oxygen ions are transported from the measured gas to the reference gas. A possible excess can flow to the ambient air via the channel 5.

Figure 4:
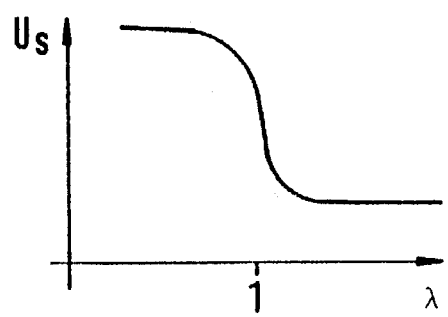
FIG. 4 is a graph of the output signal of the arrangement of FIG. 3 as it occurs in dependence upon the oxygen content in the exhaust gas with the output signal being plotted as a function of the air number $\lambda$ of the fuel/air mixture supplied to the engine.

FIG. 4 shows the measuring signal of this arrangement as a function of the oxygen concentration in the measured gas which is here exemplified by the air number λ of the fuel/air mixture for an internal combustion engine.

Figure 5:
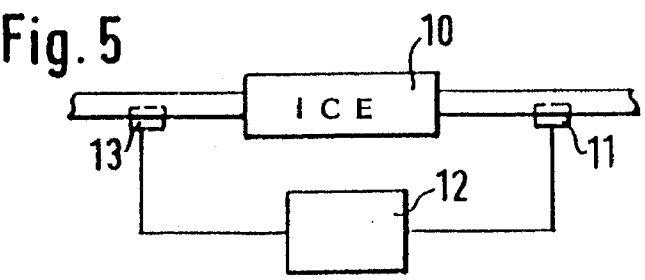
FIG. 5 is a schematic showing the application of the measuring sensor of the invention for controlling the mixture composition of an internal combustion engine; and, FIG. 6a and 6b disclose further embodiments of the measuring sensor according to the invention.

FIG. 5 is a schematic of a control loop for the air number λ while utilizing the following: the measuring sensor 11 of the invention, a controller 12 and a positioning element 13 such as a fuel-injection valve.

Figure 6A:
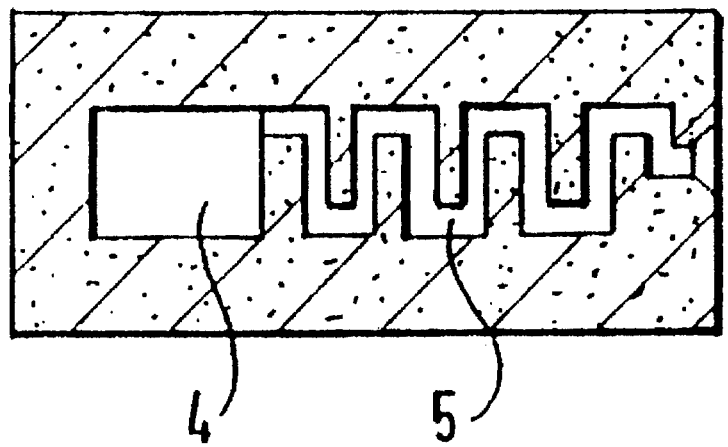
Figure 6B:
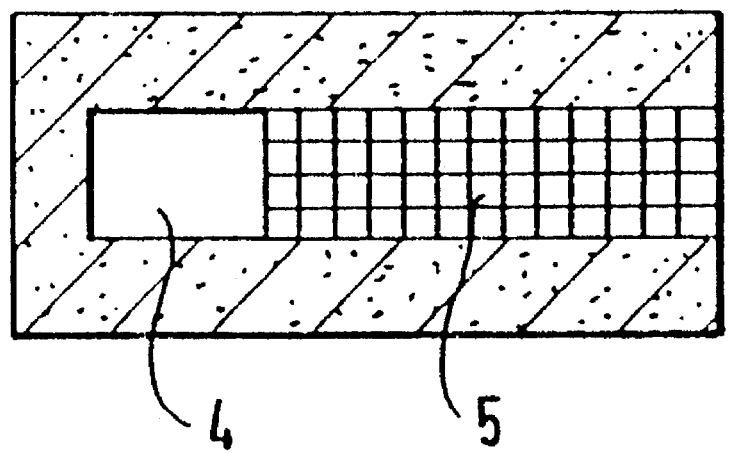

FIG. 6a shows a meander-shaped channel 5 as another embodiment of the means for compensating for overpressure and FIG. 6b shows a printed lattice as a means for overpressure compensation.

The embodiments can be combined with each other. For example, each geometric structure can be filled with a porous mass having a resistance which can be considered when constructing the measuring sensor. The resistance is adjusted via the pore size.

It is understood that the foregoing description is that of the preferred embodiments of the invention and that various changes and modifications may be made thereto without departing from the spirit and scope of the invention as defined in the appended claims.

What is claimed is:

1. A measuring sensor for determining the concentration of oxygen in a gas to be measured or measured gas, the measuring sensor comprising:

a solid electrolyte;

a measuring electrode arranged on said electrolyte to be subjected to said measured gas;

a reference electrode arranged on said electrolyte;

said solid electrolyte having an internal reference gas volume formed therein to communicate directly with said reference electrode;

electric voltage means for applying a voltage of a first polarity across said electrodes during measurement for determining the concentration of oxygen in said measured gas by causing an oxygen ion flow from said measured gas into said internal reference gas volume thereby pumping oxygen from said measured gas into said internal reference gas volume to supply the reference gas;

overpressure compensating means interposed between said internal reference gas volume and said ambient air for defining a diffusion resistance means for facilitating the movement of oxygen only from said internal reference gas volume to the ambient when there is an overpressure of oxygen in said internal reference gas volume; and, said diffusion resistance means having dimensions of structure which cause said diffusion resistance means to provide a resistance to particle flow from the ambient to said internal reference gas volume which corresponds to a diffusion limit current having a current intensity of 0.5 to 50 microampere which current intensity is measured when said sensor is not in use by applying a voltage of a second polarity across said electrodes opposite said first polarity.

2. The measuring sensor of claim 1, wherein said diffusion resistance means is configured to provide a diffusion limit current having a current intensity of 1 to 10 microampere which current intensity is measured when said sensor is not in use by applying a voltage of a second polarity across said electrodes opposite said first polarity.

3. The measuring sensor of claim 1, said overpressure compensating means comprising a thin channel formed in said electrolyte and extending between said holding means and the ambient; and, porous material filling said channel.

4. The measuring sensor of claim 1, wherein said overpressure compensating means is a porous electrode input lead.

5. A control loop for an internal combustion engine supplied with a fuel/air mixture and generating exhaust gas as the fuel/air mixture is consumed, the control loop comprising:

a measuring sensor for determining the concentration of oxygen in said exhaust gas and for supplying an output signal indicative of said concentration;

controller means for controlling said fuel/air mixture supplied to said engine on the basis of said output signal; and, said measuring sensor including:

a solid electrolyte;

a measuring electrode arranged on said electrolyte to be subjected to said measured gas;

a reference electrode arranged on said electrolyte;

said solid electrolyte having an internal reference gas volume formed therein to communicate directly with said reference electrode;

electric voltage means for applying a voltage of a first polarity across said electrodes during measurement for determining the concentration of oxygen in said measured gas by causing an oxygen ion flow from said measured gas into said internal reference gas volume thereby pumping oxygen from said measured gas into said internal reference gas volume to supply the reference gas;

overpressure compensating means interposed between said internal reference gas volume and said ambient air for defining a diffusion resistance means for facilitating the movement of oxygen only from said internal reference gas volume to the ambient when there is an overpressure of oxygen in said internal reference gas volume; and, said diffusion resistance means having dimensions of structure which cause said diffusion resistance means to provide a resistance to particle flow from the ambient to said internal reference gas volume which corresponds to a diffusion limit current having a current intensity of 0.5 to 50 microampere which current intensity is measured when said sensor is not in use by applying a voltage of a second polarity across said electrodes opposite said first polarity.

* * * * *